(12) United States Patent
Hagiwara et al.

(10) Patent No.: US 7,076,019 B2
(45) Date of Patent: Jul. 11, 2006

(54) RADIATION COMPUTED TOMOGRAPHY APPARATUS

(75) Inventors: Akira Hagiwara, Tokyo (JP); Kotoko Morikawa, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1 day.

(21) Appl. No.: 10/828,456

(22) Filed: Apr. 20, 2004

(65) Prior Publication Data

US 2004/0208278 A1 Oct. 21, 2004

(30) Foreign Application Priority Data

Apr. 21, 2003 (JP) ............................. 2003-115412

(51) Int. Cl.
*A61B 6/03* (2006.01)
(52) U.S. Cl. ............................................. 378/16; 378/4
(58) Field of Classification Search .................... 378/4, 378/16, 19, 150, 151, 901
See application file for complete search history.

(56) References Cited

U.S. PATENT DOCUMENTS

| 5,727,041 | A | 3/1998 | Hsieh | 378/4 |
|---|---|---|---|---|
| 5,812,628 | A | 9/1998 | Hsieh | 378/8 |
| 5,970,112 | A | 10/1999 | Hsieh | 378/8 |
| 6,023,494 | A | 2/2000 | Senzig et al. | 378/4 |
| 6,061,421 | A | 5/2000 | Hagiwara | 378/4 |
| 6,320,929 | B1 | 11/2001 | Von Der Haar | 378/4 |
| 6,445,764 | B1 | 9/2002 | Gohno et al. | 378/19 |
| 6,507,642 | B1 * | 1/2003 | Fujishige et al. | 378/151 |

FOREIGN PATENT DOCUMENTS

| EP | 1216662 A2 | 6/2002 |
|---|---|---|
| JP | 2001-161678 | 6/2001 |

OTHER PUBLICATIONS

Search Report, European App. No. 04 252 252.4, Sep. 27, 2004, 3 pgs.

* cited by examiner

*Primary Examiner*—Courtney Thomas
(74) *Attorney, Agent, or Firm*—Carl B. Horton, Esq.; Armstrong Teasdale LLP (57) ABSTRACT

An X-ray CT apparatus including an X-ray tube, a detector array including a plurality of detector rows along the axis of rotation, and a reconstructing section for calculating and reconstructing tomographic image data of a subject based on the acquired projection data. The CT apparatus also includes a collimator for adjusting the emission extent of the X-rays from the X-ray tube in response to a control command, and a control section for calculating detector rows required for acquiring the projection data for use in reconstruction of a certain portion of the tomographic image data based on parameters relating to reconstruction of the tomographic image data by the reconstructing section, and outputting the control command to the collimator for emitting the X-rays to impinge upon the calculated detector rows.

16 Claims, 8 Drawing Sheets

RADIATION COMPUTED TOMOGRAPHY APPARATUS

CROSS REFERENCE TO RELATED APPLICATIONS

This application claims the benefit of Japanese Application No. 2003-115412 filed Apr. 21, 2003.

BACKGROUND OF THE INVENTION

The present invention relates to a radiation computed tomography apparatus (referred to as a radiation CT apparatus hereinbelow) for calculating a tomographic image of a subject from radiation projection data on the subject.

Known radiation CT apparatuses include an X-ray CT apparatus employing X-rays as radiation, for example. Known X-ray CT apparatuses include an apparatus comprising a plurality of X-ray detectors arranged in a two-dimensional manner. The plurality of X-ray detectors are disposed to have a width in a direction along a predefined axis with respect to a subject. Since rows of X-ray detectors are formed in the axis direction in the predefined width, the X-ray detectors arranged in a two-dimensional manner are generally referred to as a multi-row detector.

One known technique for reconstructing a tomographic image employing the multi-row detector is a cone BP (backprojection) process (see Patent Document 1, for example). In the cone BP process, a scan generally referred to as a helical scan is conducted, in which X-rays passing through a region to be examined in a subject are detected by, for example, rotating the multi-row detector around the aforementioned axis while moving the multi-row detector relative to the subject in the axis direction.

Production of a tomographic image corresponding to a row of the X-ray detectors by the cone BP process uses not only detected data obtained by that row of X-ray detectors but those from X-rays passing through the region to be examined corresponding to the tomographic image and detected by the other rows of X-ray detectors.

[Patent Document 1]
Japanese Patent Application Laid Open No. 2001-161678.

When conducting the helical scan and conducting the cone BP process, if the helical pitch is smaller than a certain value, there is a possibility that some detected data are not used in reconstructing a tomographic image. The helical pitch is a value derived from the relationship between the width of the multi-row detector in a direction along the axis and the distance of movement of the subject relative to the multi-row detector during one rotation of the multi-row detector.

If some detected data are not used in reconstructing a tomographic image, X-rays for acquiring such non-used detected data are uselessly emitted.

SUMMARY OF THE INVENTION

It is therefore an object of the present invention to provide a CT apparatus that can efficiently use radiation in collecting projection data employing a multi-row detector.

A radiation computed tomography apparatus of a first aspect of the present invention comprises: a radiation source for emitting radiation toward a subject; adjusting means for adjusting an emission extent of the radiation from said radiation source in response to a control command; a detector array forming a two-dimensional radiation detection surface comprised of a plurality of radiation detectors, for detecting the radiation on said radiation detection surface; reconstructing means for calculating and reconstructing tomographic image data for a tomographic image of said subject based on projection data of said subject by the radiation acquired by said detector array; and control means for calculating an irradiated region in said radiation detection surface required for acquiring said projection data for use in reconstruction of a certain portion of said tomographic image data based on parameters relating to reconstruction of said tomographic image data by said reconstructing means, and outputting said control command to said adjusting means for emitting the radiation to impinge upon said irradiated region.

A radiation computed tomography apparatus of a second aspect of the present invention comprises a radiation source for emitting radiation having a predefined width toward a subject, and a detector array forming a two-dimensional radiation detection surface comprised of a plurality of radiation detectors, for detecting the radiation on said radiation detection surface, said apparatus for calculating and reconstructing tomographic image data for a tomographic image of said subject based on projection data of said subject by the radiation from said radiation source acquired by said detector array, and said apparatus further comprises: processing means for, in reconstruction of said tomographic image data, determining the number of times of use of said projection data from each of said plurality of radiation detectors based on parameters relating to reconstruction of said tomographic image data.

In the radiation computed tomography apparatus of the first aspect of the present invention, radiation is emitted from a radiation source toward a subject. An emission extent of the radiation is adjusted by adjusting means receiving a control command. The radiation having the adjusted emission extent is detected on a radiation detection surface formed in a two-dimensional manner on a detector array comprised of a plurality of radiation detectors. By thus detecting the radiation by the detector array, projection data of the subject by the radiation is acquired. Reconstructing means calculates and reconstructs tomographic image data of the subject based on the projection data.

In acquiring the projection data by the detector array, an irradiated region in the radiation detection surface required for acquiring the projection data for use in reconstruction of a certain portion of the tomographic image data is calculated by the control means based on parameters relating to reconstruction of the tomographic image data. Control means outputs the control command to the adjusting means for emitting the radiation to impinge upon the irradiated region.

In the radiation computed tomography apparatus of the second aspect of the present invention, radiation having a predefined width is emitted from a radiation source toward a subject. The radiation having the predefined width is detected on a radiation detection surface formed in a two-dimensional manner on a detector array. By thus detecting the radiation by the detector array, projection data of the subject by the radiation is acquired. Based on the projection data, tomographic image data of the subject is calculated and reconstructed.

The number of times of use of the projection data in the reconstruction of the tomographic image data is determined by processing means based on parameters relating to reconstruction of the tomographic image data.

According to the present invention, there is provided a CT apparatus that can efficiently use radiation in collecting projection data using a multi-row detector.

Further objects and advantages of the present invention will be apparent from the following description of the preferred embodiments of the invention as illustrated in the accompanying drawings.

DETAILED DESCRIPTION OF THE INVENTION

Embodiments of the present invention will now be described with reference to the accompanying drawings. Radiation in the present invention includes X-rays. The embodiments below will be described regarding an X-ray CT apparatus as an example of the radiation CT apparatus.

FIRST EMBODIMENT

Figure 1:
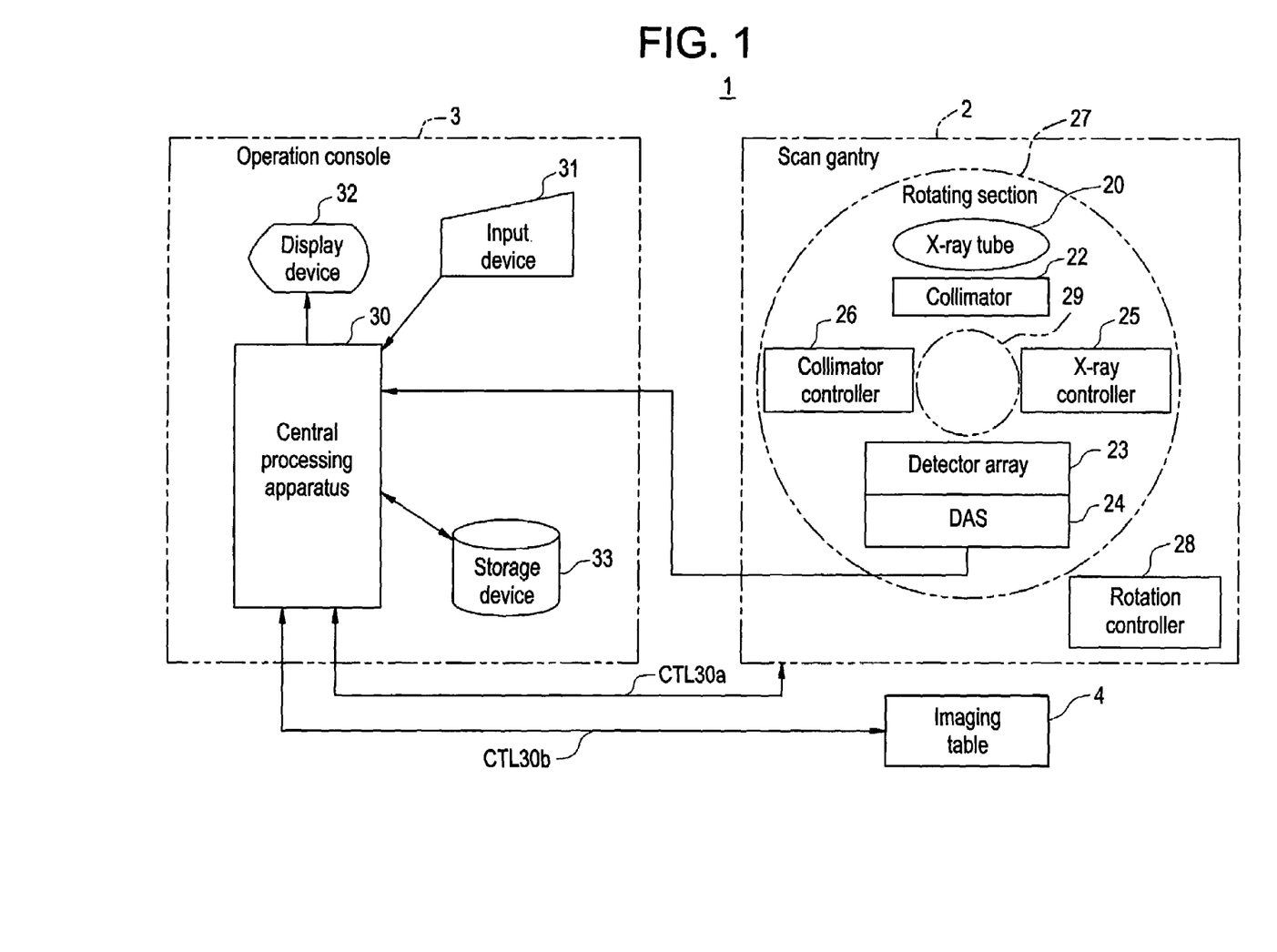
FIG. 1 shows the apparatus configuration of an X-ray CT apparatus in accordance with a first embodiment of the present invention.
Figure 2:
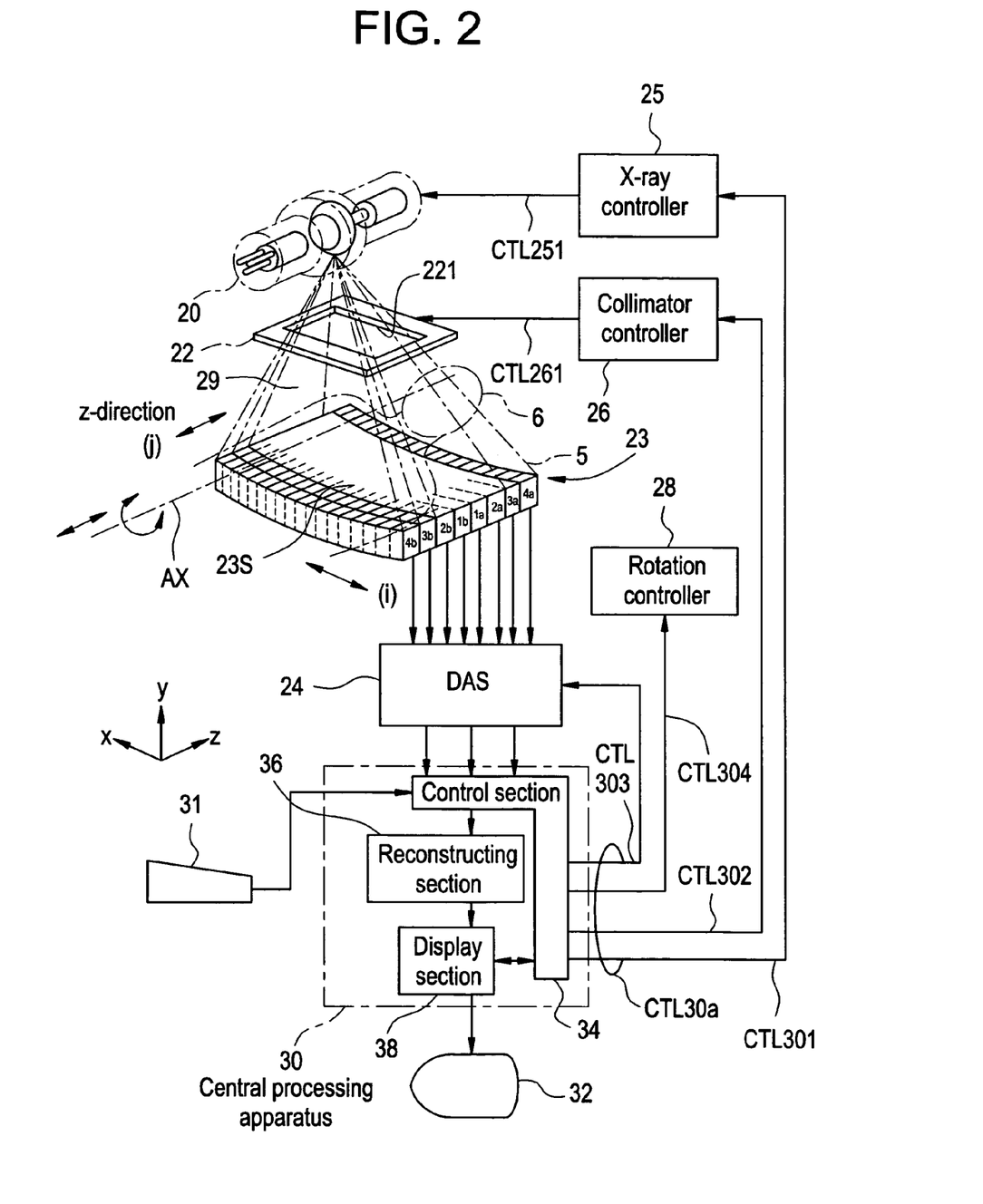
FIG. 2 shows the configuration of a main portion in the X-ray CT apparatus shown in FIG. 1.

FIG. 1 shows the apparatus configuration of an X-ray CT apparatus in accordance with a first embodiment of the present invention, and FIG. 2 shows the configuration of a main portion in the X-ray CT apparatus shown in FIG. 1. The X-ray CT apparatus 1 shown in FIG. 1 is one embodiment of the radiation computed tomography apparatus in the present invention.

As shown in FIG. 1, the X-ray CT apparatus 1 comprises a scan gantry 2, an operation console 3, and an imaging table 4.

The scan gantry 2 comprises an X-ray tube 20, a collimator 22, a detector array 23, a data acquisition system (DAS) 24, an X-ray controller 25, a collimator controller 26, a rotating section 27, and a rotation controller 28.

The X-ray tube 20 is one embodiment of the radiation source and the collimator 22 is one embodiment of the adjusting means in the present invention. The imaging table 4, rotating section 27 and rotation controller 28 constitute one embodiment of the moving means in the present invention.

As shown in FIG. 2, the X-ray controller 25 is connected to the X-ray tube 20, and the collimator controller 26 is connected to the collimator 22. The detector array 23 is connected to the DAS 24, and the rotation controller 28 is connected to the rotating section 27.

The X-ray tube 20 emits X-rays at a certain intensity toward the collimator 22 based on a control signal CTL251 from the X-ray controller 25.

The collimator 22 adjusts the emission extent of the X-rays emitted by the X-ray tube 20 through adjustment of the degree of openness of an aperture 221 based on a control signal CTL261 from the collimator controller 26.

The detector array 23 employs a plurality of X-ray detectors to form a two-dimensional matrix (array) having i columns and j rows.

Each X-ray detector is made of a combination of a scintillator and a photodiode, for example.

In the column direction, approximately i=1000 X-ray detectors are arranged to constitute one detector row. FIG. 2 shows the detector array 23 having, by way of example, eight detector rows, i.e., j=8. The detector rows are designated hereinbelow as detector rows 1a, 2a, 3a and 4a sequentially from the center to the right in the row direction of the detector array 23, and as detector rows 1b, 2b, 3b and 4b sequentially from the center to the left.

The plurality of detector rows 1a–4a and 1b–4b are adjoined in parallel with one another.

By thus arranging the X-ray detectors in a matrix, a generally two-dimensional X-ray detection surface 23S is formed.

As shown in FIGS. 1 and 2, the detector array 23 is disposed at a certain distance from the collimator 22. The space between the collimator 22 and detector array 23 forms an X-ray emission space 29. The X-ray emission space 29 receives a subject 6.

The detector array 23 detects on the X-ray detection surface 23S the intensity of X-ray beams 5 emitted at the aperture 221 of the collimator 22 and passing through the X-ray emission space 29 receiving therein the subject 6.

The DAS 24 collects detected data for the X-ray intensity from the individual X-ray detectors constituting the X-ray detection surface 23S based on a control signal CTL303 from the operation console 3, and sends the data to the operation console 3.

The DAS 24 A-D (analog-to-digital) converts the detected data collected and sends it to the operation console 3. The data sent by the DAS 24 is sometimes referred to as raw data.

The rotating section 27 rotates around a predefined axis of rotation AX of the X-ray emission space 29 based on a control signal from the rotation controller 28.

The rotating section 27 supports the X-ray tube 20, collimator 22, detector array 23, DAS 24, X-ray controller 25 and collimator controller 26, and rotates together around the axis of rotation AX by rotation of the rotating section 27 while maintaining the relative positional relationship among these components.

In the present embodiment, the detector rows in the detector array 23 are arranged in the direction of the axis of rotation AX. The direction of the axis of rotation AX, i.e., the direction of the arrangement of the detector rows 1a–4a and 1b–4b in the detector array 23, is defined as a z-direction.

The X-ray tube 20 and detector array 23 are disposed so that the emission center of X-rays in the X-ray tube 20 is aligned with the center of the detector array 23 in the z-direction.

The position of the imaging table 4 can be changed by driving means such as a motor, which is not shown. The subject 6 is laid on the imaging table 4. The position of the imaging table 4 is changed in response to a control signal CTL30b from the operation console 3 when carrying the subject 6 into the X-ray emission space 29 or when imaging the subject 6.

The subject 6 is carried into the X-ray emission space 29 so that the direction of the subject's body axis running from head to toe is aligned with the z-direction, for example. The X-ray tube 20 and detector array 23 are thus moved in the z-direction relative to the subject 6.

The X-ray controller 25 outputs the control signal CTL251 to the X-ray tube 20 for controlling the intensity of the X-rays emitted by the X-ray tube 20 based on a control signal CTL301 from the central processing apparatus 30 in the operation console 3, which will be discussed later.

The collimator controller 26 controls the degree of openness of the aperture 221 by the control signal CTL261 output to the collimator 22 in response to a control signal CTL302 from the operation console 3.

The rotation controller 28 outputs a control signal to the rotating section 27 based on a control signal CTL304 from the central processing apparatus 30 in the operation console 3 to rotate the rotating section 27 around the axis of rotation AX.

As shown in FIG. 1, the operation console 3 comprises a central processing apparatus 30, an input device 31, a display device 32, and a storage device 33.

The input device 31 accepts a command input by an operator for operating the X-ray CT apparatus 1, and sends the command to the central processing apparatus 30.

The display device 32 is for displaying a CT image resulting from a calculation by the central processing apparatus 30.

The storage device 33 stores several kinds of programs and parameters for operating the X-ray CT apparatus 1 via the central processing apparatus 30, and data including image data for a CT image.

As shown in FIG. 2, the central processing apparatus 30 comprises a control section 34, a reconstructing section 36, and a display section 38.

The reconstructing section 36 is one embodiment of the reconstructing means and the control section 34 is one embodiment of the control means in the present invention.

The central processing apparatus 30 may be constituted as a single hardware unit or as a system comprised of a plurality of appropriate hardware units corresponding to the aforementioned components.

The control section 34 is connected with the DAS 24, input device 31, reconstructing section 36, display section 38, X-ray controller 25, collimator controller 26, rotation controller 28 and imaging table 4.

The reconstructing section 36 is further connected to the display section 38.

The storage device 33 is appropriately accessed by the control section 34, reconstructing section 36 and display section 38.

The control section 34 outputs the control signal CTL30b to the imaging table 4 to carry the subject 6 in the z-direction.

The control section 34 outputs a control signal CTL30a to the scan gantry 2 based on a command input by the operator via the input device 31 for acquiring detected data for use in producing a tomographic image of the subject 6 as a CT image, and causes the gantry 2 to conduct a scan on the subject 6. A method of scanning the subject 6 will be discussed later.

The control signal CTL30a from the control section 34 includes the control signals CTL301, 302, 303 and 304.

Furthermore, the control section 34 receives the raw data based on the detected data collected by the DAS 24 in a scan. The data received by the control section 34 is projection data of the subject 6 by the radiation.

The reconstructing section 36 obtains the projection data via the control section 34. The reconstructing section 36 then performs arithmetic processing including backprojection processing known in the art on the obtained projection data to reconstruct a tomographic image of a region to be examined in the subject 6.

The display section 38 displays the tomographic image produced by the reconstructing section 36 on the display device 32 in response to a command signal from the control section 34.

Now an operation of the X-ray CT apparatus 1 in accordance with the first embodiment will be described.

The control section 34 outputs the control signals CTL30b and CTL304 to the imaging table 4 and rotation controller 28, respectively, to move the imaging table 4 in the z-direction while rotating the rotating section 27 around the axis of rotation AX, for acquiring projection data for use in image production. From the viewpoint of the subject 6 lying on the imaging table 4, the X-ray tube 20, collimator 22 and detector array 23 mounted on the rotating section 27 appear to helically move around the axis of rotation AX. The DAS 24 collects detected data at predetermined sampling intervals during the rotation of the rotating section 27. The acquisition of the projection data through such helical movement is referred to as helical scanning.

Figure 3:
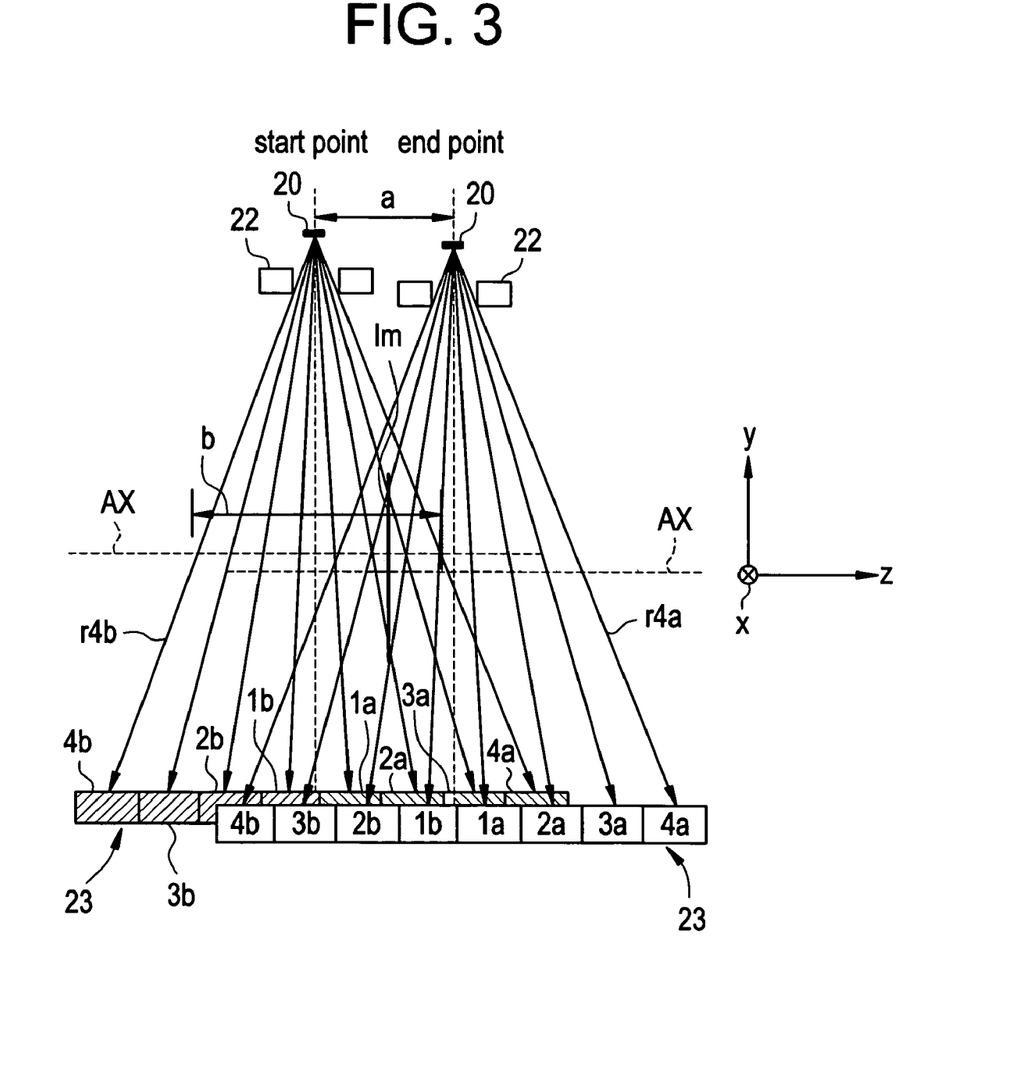
FIG. 3 shows the relationship between a tomographic image obtained in the first embodiment of the present invention and X-ray beams.

FIG. 3 shows the relationship between a tomographic image obtained in the first embodiment and X-ray beams. In FIG. 3, a plane containing the axis of rotation AX, X-ray tube 20, collimator 22 and detector array 23 at the initial position is defined as the yz-plane. A direction orthogonal to the yz-plane in the drawing paper plane is the x-direction.

Moreover, in FIG. 3, the X-ray tube 20, collimator 22 and detector array 23 conducting a helical scan at the initial position and at the position after one rotation around the axis of rotation AX relative to the subject 6 are shown. For convenience of understanding, the X-ray tube 20, collimator 22, detector array 23 and axis of rotation AX are depicted as being offset between the initial position and the position after one rotation.

The initial position of the X-ray tube 20 relative to the subject 6 will be sometimes referred to as the start point, and the position after one rotation as the end point hereinbelow.

In the first embodiment, the reconstructing section 36 reconstructs a tomographic image based on detected data in one rotation of the rotating section 27. Moreover, consideration is made on a case in which the reconstructing section 36 reconstructs image data for a tomographic image Im parallel to the xy-plane at a midpoint between the start point and the end point at a distance a by way of example.

Furthermore, consideration is made on a case in which the helical pitch in the helical scan is one or less. FIG. 8 is a diagram for explaining the definition of the helical pitch, in which (a) shows a helical pitch of about one, and (b) shows a helical pitch less than one.

Figure 8A:
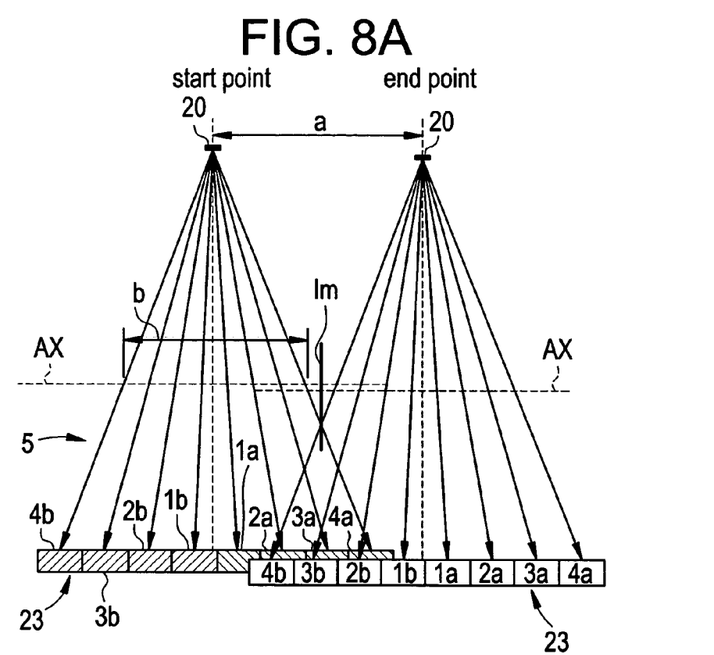
FIG. 8 is for explaining the definition of a helical pitch, in which (a) shows a helical pitch of about one, and (b) shows a helical pitch less than one.
Figure 8B:
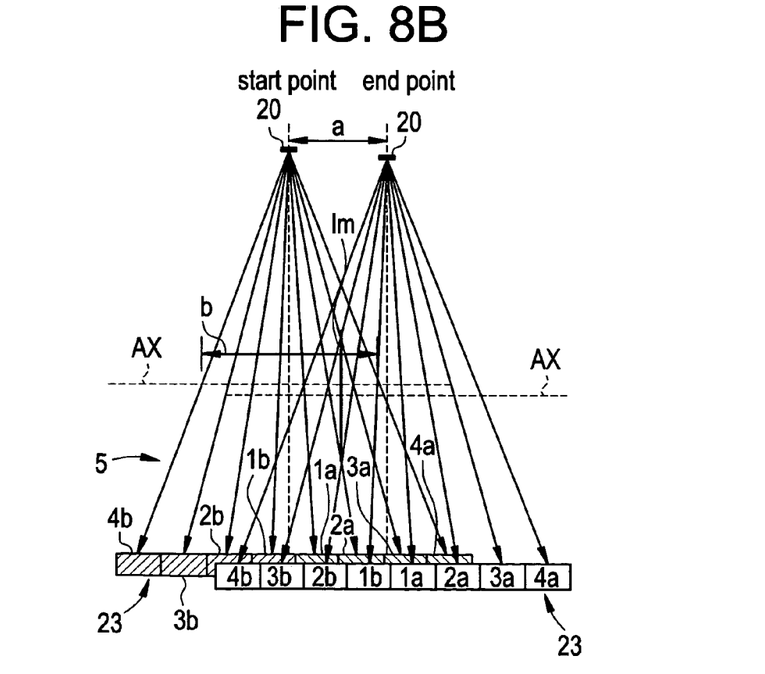

FIGS. 8(a) and (b) are similar to FIG. 3, and show the positional relationship of the X-ray tube 20 and detector array 23 relative to the subject 6 during one rotation around the axis of rotation AX, in a plane containing the axis of rotation AX.

The relative movement distance between the X-ray tube 20/detector array 23 and the subject 6 along the axis of rotation AX is defined as a. Moreover, the emission width of the X-ray beams 5 on the axis of rotation AX when the X-ray beams 5 impinge upon all the detector rows in the detector array 23 is defined as b.

In the present embodiment, the helical pitch hp is defined as hp=a/b.

In FIG. 8(a), a≈b, and the helical pitch is about one.

In FIG. 8(b), a<b, and the helical pitch is less than one.

The helical pitch is thus determined by the geometrical positional relationship (geometry) of the X-ray tube 20, axis of rotation AX and detector array 23, the number of detector rows in the detector array 23, and the movement speed of the imaging table 4.

When the helical pitch is less than one as shown in FIG. 3, there is a possibility that some detector rows are not used in reconstruction of the tomographic image Im.

For example, when reconstructing the tomographic image Im shown in FIG. 3, only X-ray beams impinging upon the detector rows 2a and 3a pass through the region to be examined corresponding to the tomographic image Im at the start point. At the end point, only X-ray beams impinging upon the detector rows 2b and 3b pass through the region to be examined corresponding to the tomographic image Im.

Consequently, it can be seen that in reconstructing the tomographic image Im, only detected data of X-rays impinging upon the detector rows 2a, 3a, 2b and 3b are used during one rotation of the rotating section 27, and the detector rows 4a and 4b are not needed in reconstructing the tomographic image Im.

It is obvious that detector rows required for acquiring detected data for use in reconstruction of a tomographic image vary according to parameters including, for example, the size of the tomographic image Im, the position of the tomographic image Im in the y-direction and z-direction, the geometry of the X-ray tube 20, axis of rotation AX and detector array 23, the number of detector rows, and the helical pitch.

It can be seen from FIG. 3 that in reconstructing the tomographic image Im at the midpoint between the start and end points, the outer detector rows in the z-direction tend not to be used for the tomographic image Im having the center in the y-direction nearer to the axis of rotation AX, the smaller size of the tomographic image Im, and the smaller helical pitch.

Among the parameters relating to reconstruction of image data for the tomographic image Im, the geometry and the number of detector rows are invariable because they depend upon the apparatus configuration of the gantry 2, and their information is saved in the storage device 33.

The size of the tomographic image Im, its position relative to the axis of rotation AX, and the helical pitch are parameters that can be arbitrarily specified by the operator in imaging. The operator inputs these parameters via the input device 31. The input parameters are sent to the storage device 33 via the central processing apparatus 30, and stored in the storage device 33.

The control section 34 accesses the storage device 33 in a scan for acquiring projection data to obtain the parameters relating to reconstruction of image data for the tomographic image Im. The control section 34 then arithmetically finds detector rows required for acquiring projection data for use in reconstruction of the image data for the tomographic image Im based on these parameters. Specifically, for example, detector rows required for acquiring projection data for the tomographic image Im shown in FIG. 3 are arithmetically found to be detector rows 2a, 3a, 2b and 3b as described above. The detector rows required for acquiring projection data are thus found from the geometrical relationship based on the parameters relating to reconstruction of image data.

The control section 34 outputs the control signal CTL302 to the collimator controller 28 in a helical scan to emit X-rays to constantly impinge upon the detector rows 2a, 3a, 2b and 3b required for acquiring projection data for use in reconstruction of image data for the tomographic image Im.

The control signal CTL261 from the collimator controller 28 adjusts the degree of openness of the aperture 221 in the collimator 22 to prevent X-ray beams r4a and r4b from impinging upon the detector row 4a and 4b, and X-rays are emitted to impinge upon only a range of the detector rows 2a, 3a, 2b and 3b.

An image reconstruction procedure in the first embodiment will be summarized below with reference to a flow chart shown in FIG. 4.

First, the operator inputs parameters relating to imaging, such as the position and size of a tomographic image Im to be obtained, and the helical pitch (Step ST1).

The parameters relating to imaging are sent to the storage device 33, and stored together with parameters relating to the apparatus configuration including the geometry and the number of detector rows in the storage device 33 as the parameters relating to reconstruction of tomographic image data.

The control section 34 calculates detector rows required for acquiring projection data for use in reconstruction of tomographic image data for the tomographic image Im to be reconstructed based on the parameters relating to reconstruction of tomographic image data (Step ST2).

An emission extent of X-rays is adjusted so that X-rays impinge upon a region constituted by the detector rows calculated at Step ST2 (Step ST3).

The region constituted by the detector rows calculated at Step ST2 corresponds to the irradiated region of the present invention.

The adjustment of the emission extent of X-rays is achieved by the collimator. In the first embodiment, once the degree of openness of the aperture 211 has been adjusted so that X-rays impinge upon the irradiated region, the collimator 22 does not need to be controlled during the scan.

While emitting X-rays toward only the irradiated region, a helical scan is conducted (Step ST4).

Since the tomographic image Im is reconstructed from detected data acquired during one rotation of the rotating section 27 in the present embodiment, the scan is terminated after the rotating section 27 has rotated by 360° around the axis of rotation AX from the start point.

The reconstructing section 36 reconstructs image data for the tomographic image Im based on the projection data obtained in the helical scan at Step ST4 (Step ST5).

In reconstructing the tomographic image data, the cone BP process known in the art is employed, for example.

The tomographic image Im having the image data reconstructed by the calculation by the reconstructing section 36 is displayed on the display device 32 as needed.

As described above, according to the first embodiment, based on parameters relating to reconstruction of tomographic image data at a certain position, detector rows required for acquiring projection data for use in reconstruction of the tomographic image data are automatically calculated. A scan is then conducted so that X-rays impinge upon the calculated detector rows. X-ray beams are prevented from impinging upon detector rows other than the calculated detector rows by the collimator 22. Thus, X-ray beams are prevented from impinging upon detector rows that do not contribute to tomographic image data reconstruction, thereby eliminating useless X-ray beam emission. As a result, the exposure dose to the subject 6 can be reduced. These effects are more remarkable for a smaller helical pitch.

SECOND EMBODIMENT

In the first embodiment, X-rays are emitted to constantly impinge upon the irradiated region calculated once during a scan. In a second embodiment of the present invention described below, a region within the irradiated region upon which X-rays impinge is further modulated during a scan.

Figure 5:
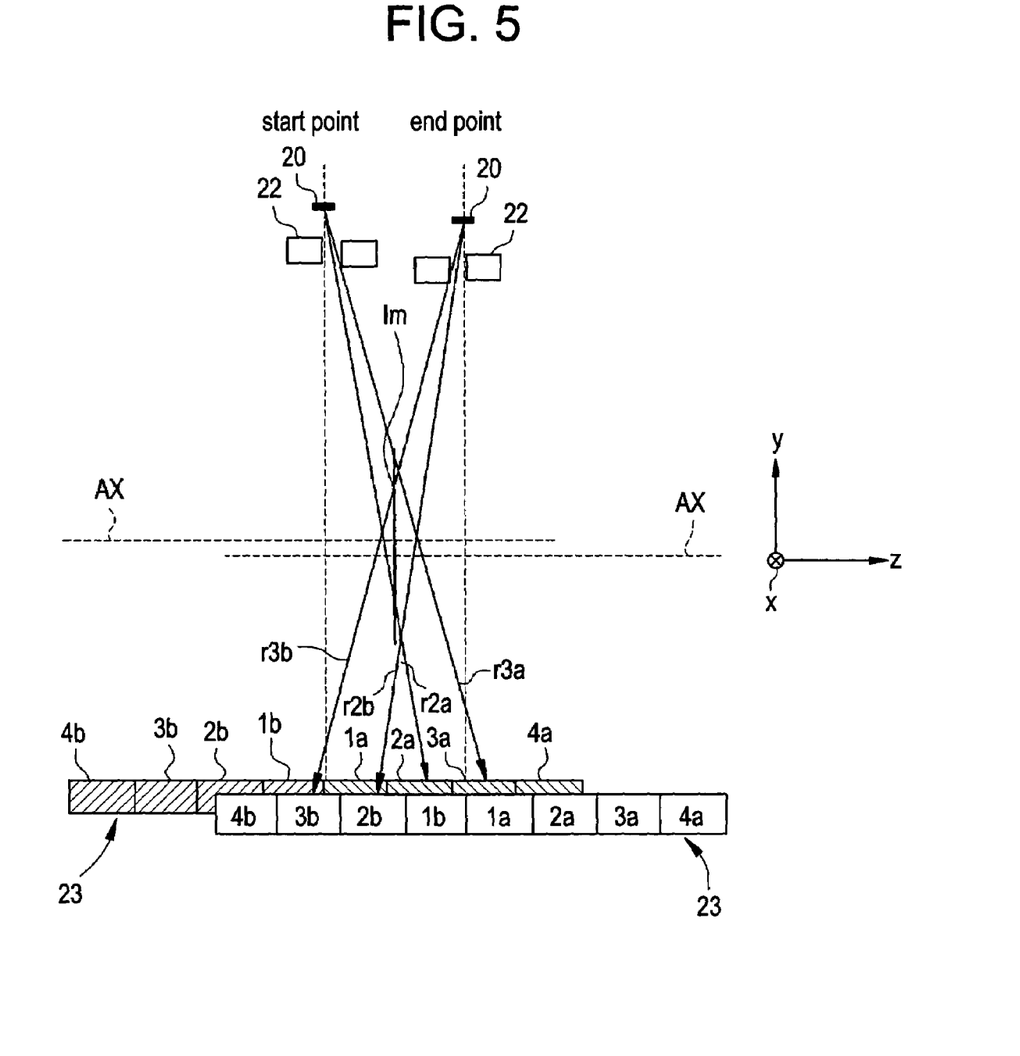
FIG. 5 shows the relationship between a tomographic image obtained in a second embodiment of the present invention and X-ray beams.

FIG. 5 shows the relationship between a tomographic image obtained in the second embodiment and X-ray beams. FIG. 5 is similar to FIGS. 3 and 8, and shows the positional relationship of the X-ray tube 20 and detector array 23 relative to the subject 6 during one rotation around the axis of rotation AX, in a plane containing the axis of rotation AX.

The X-ray CT apparatus of the second embodiment is similar to the X-ray CT apparatus 1 in accordance with the first embodiment except that a region upon which X-rays impinge is modulated during a scan. Therefore, detailed description on the apparatus configuration is omitted.

In FIGS. 5 and 3, the helical pitch is the same. It is assumed that a tomographic image Im having the same size and at the same position as in the first embodiment is to be reconstructed.

As described regarding the first embodiment, at the start point, only X-ray beams r2a and r3a impinging upon the detector rows 2a and 3a pass through a region to be examined corresponding to the tomographic image Im. At the end point, only X-ray beams r2b and r3b impinging upon the detector rows 2b and 3b pass through the region to be examined corresponding to the tomographic image Im.

While detector rows required for acquiring projection data for use in reconstruction of image data for the tomographic image Im are, for example, detector rows 2a, 3a, 2b and 3b, those among these detector rows upon which radiation impinges passing through the subject in a region corresponding to the tomographic image Im successively vary with the position of the rotating section 27.

In the second embodiment, detector rows upon which radiation impinges passing through the subject in a region corresponding to the tomographic image Im are calculated by the control section 34 according to the position of the rotating section 27. A region constituted by the detection surface of the X-ray detectors in the calculated detector rows corresponds to the partial irradiated region of the present invention. The detector rows constituting the partial irradiated region can be geometrically found from the parameters relating to reconstruction of image data for the tomographic image Im mentioned in the first embodiment, and the position of the rotating section 27 relative to the subject 6.

The control section 34 outputs a control signal CTL302 to the collimator controller 26 for successively modulating the aperture 221 in the collimator 22 so that X-rays impinge upon the partial irradiated region at a position varying during a scan.

For example, as shown in FIG. 5, X-rays impinge only upon the detector rows 2a and 3a and no X-rays impinge upon the detector rows 1a, 4a, 1b–4b at the start point. At the end point, X-rays impinge only upon the detector rows 2b and 3b and no X-rays impinge upon the detector rows 1b, 4b, 1a–4a.

An image reconstruction procedure in the second embodiment is similar to that in the first embodiment except in the points described below, and detailed description will therefore be omitted.

Figure 4:
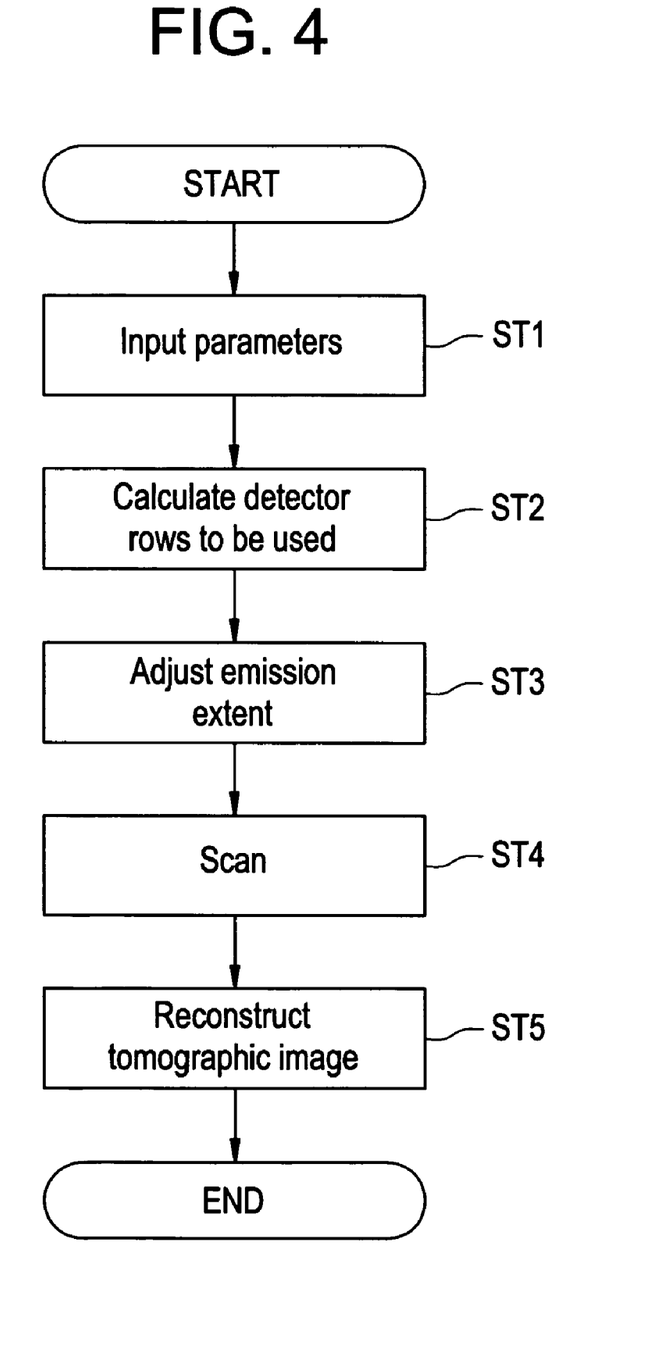
FIG. 4 is a flow chart showing an image reconstruction procedure in accordance with the first embodiment of the present invention.

In the second embodiment, detector rows corresponding to a partial irradiated region are calculated at Step ST2 in the flow chart shown in FIG. 4. Then, at Step ST3, an X-ray emission extent is adjusted in real-time so that the X-rays impinge upon the calculated detector rows, and at the same time, a scan at Step ST4 is conducted.

As described above, in the second embodiment, since X-rays do not impinge upon detector rows other than those corresponding to a partial irradiated region, useless emission of the X-ray beams is further reduced as compared with the first embodiment. As a result, the exposure dose to the subject 6 can be further reduced as compared with the first embodiment.

In spite of a reduced X-ray emission extent during a scan as compared with the first embodiment, X-rays impinge upon detector rows required for acquiring projection data for use in reconstruction of the tomographic image Im, and therefore, the image quality of the tomographic image Im is unchanged as compared with the first embodiment.

THIRD EMBODIMENT

In a third embodiment of the present invention described below, rather than controlling the X-ray emission extent, the number of times of use of projection data in reconstruction of tomographic image data is determined based on parameters relating to reconstruction of tomographic image data.

An X-ray CT apparatus in accordance with the third embodiment differs from the X-ray CT apparatus 1 in the first and second embodiments in that the former has processing means for determining the number of times of use of projection data. The processing means can be implemented by the control section 34 or reconstructing section 36 shown in FIG. 2. In the present embodiment, the processing means is implemented by the reconstructing section 36.

Since the configuration and function of the X-ray CT apparatus other than those described above are similar to those in the preceding description, detailed description is omitted.

Also in the third embodiment, it is assumed that a tomographic image Im lying at the midpoint between the start and end points of the X-ray tube 20 along the axis of rotation AX is to be reconstructed with a helical pitch less than one, as in the first and second embodiments. In the third embodiment, however, the rotation angle of the rotating section 27 in acquiring projection data for use in reconstruction of image data for the tomographic image Im is not limited to 360°. The position of the end point of the X-ray tube 20 in the third embodiment is not a position relative to the subject 6 after one rotation of the rotating section 27 but a position relative to the subject 6 at the time of completion of a scan for acquiring projection data.

Figure 6A:
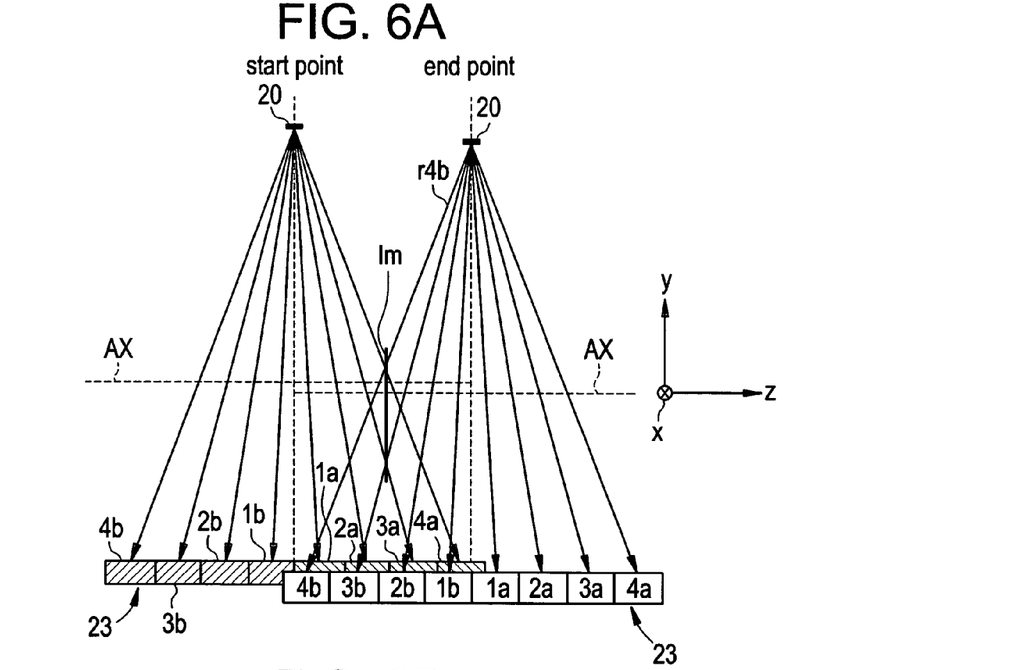
FIG. 6 shows the relationship between a tomographic image Im obtained in a third embodiment of the present invention the present invention and X-ray beams, in which (a) shows the relationship in a plane containing the axis of rotation, and (b) shows the relationship as viewed in the direction of the axis of rotation.
Figure 6B:
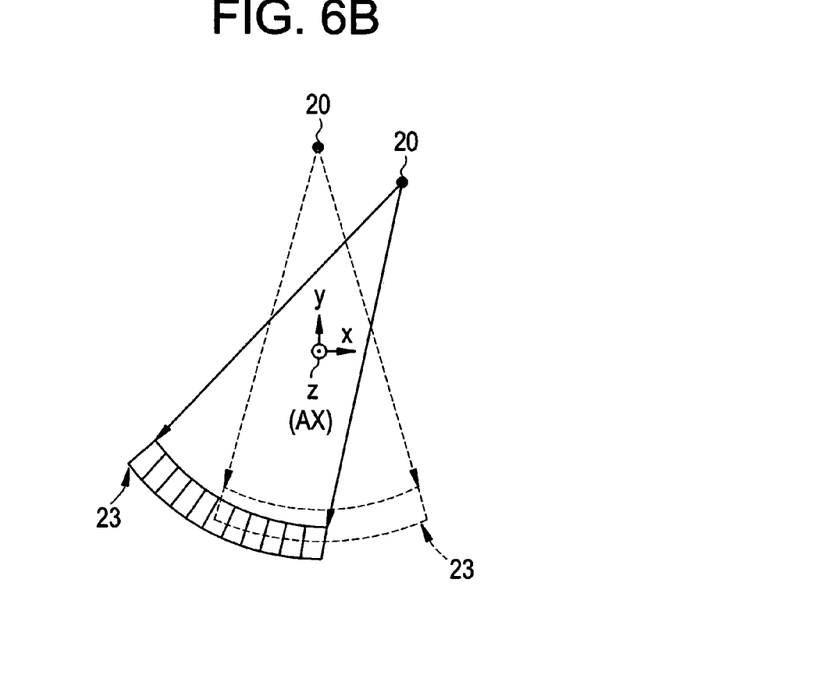

FIG. 6 shows a relationship between a tomographic image Im obtained in the third embodiment and X-ray beams. FIG. 6(a) is similar to FIGS. 3 and 5, and shows the positional relationship of the X-ray tube 20 and detector array 23 relative to the subject 6 in one scan, in a plane containing the axis of rotation AX. FIG. 6(b) shows a side view in the z-direction of FIG. 6(a).

In the present embodiment, the rotating section 27 rotates up to an angle greater than 360°, for example. Thus, at a rotation angle of the rotating section 27 other than an integer multiple of 360°, the X-ray tube 20 and detector array 23 are not in the same orientation as that at the start point, resulting in an offset in the xy-plane as shown in FIG. 6(b). However, the start and end points are drawn in the same yz-plane in FIG. 6(a) for convenience of understanding.

In the third embodiment, the control section 34 outputs a control signal CTL302 to the collimator controller 26 for emitting X-rays to impinge upon all detector rows in the detector array 23. In this condition, the control section 34 outputs control signals CTL30b and CTL304 to the imaging table 4 and rotation controller 28, respectively, to conduct a helical scan up to a rotation angle of the rotating section 27 greater than 360°.

After the rotating section 27 has rotated to an angle greater than 360°, the helical pitch is pseudo-increased, and it is possible to use projection data acquired by outer detector rows in the z-direction of the detector array 23 in reconstruction of tomographic image data, as shown in FIG. 6(a).

From which detector rows projection data can be used in reconstruction of the tomographic image Im, varies according to parameters relating to reconstruction of tomographic image data, such as the size of the tomographic image Im, the position of the tomographic image Im in the y-direction and z-direction, the geometry, the number of detector rows, and the helical pitch, as in the first and second embodiments.

The control section 34 calculates which projection data acquired by X-ray detectors in the detector array 23 is to be used to reconstruct the tomographic image Im based on these parameters. From the standpoint of projection data, this means that the number of times of use of the projection data in reconstruction of tomographic image data is determined.

For example, even if projection data is acquired from an X-ray beam r4b impinging upon the detector row 4b at the end point in FIG. 6(a), the projection data from the X-ray beam r4b is not used in reconstruction in the conventional technique that dictates the tomographic image Im to be reconstructed using only projection data during one rotation of the rotating section 27. In the present embodiment, if such projection data can be used in reconstruction, it is used to reconstruct tomographic image data. From the standpoint of projection data from the X-ray beam r4b, the number of times of use is increased.

As described above, the control section 34 determines the number of times of use of projection data acquired in a scan based on the parameters relating to reconstruction of tomographic image data. Preferably, the amount of movement of the rotating section 27 relative to the subject 6 is determined and X-rays are emitted toward detector rows so that the number of times of use determined based on the parameters relating to reconstruction of tomographic image data is reached, which is preferable in the efficiency of acquisition of projection data.

The amount of movement of the rotating section 27 for this is calculated by the control section 34. Therefore, the calculating means of the present invention is implemented by the control section 34 in the present embodiment.

Figure 7:
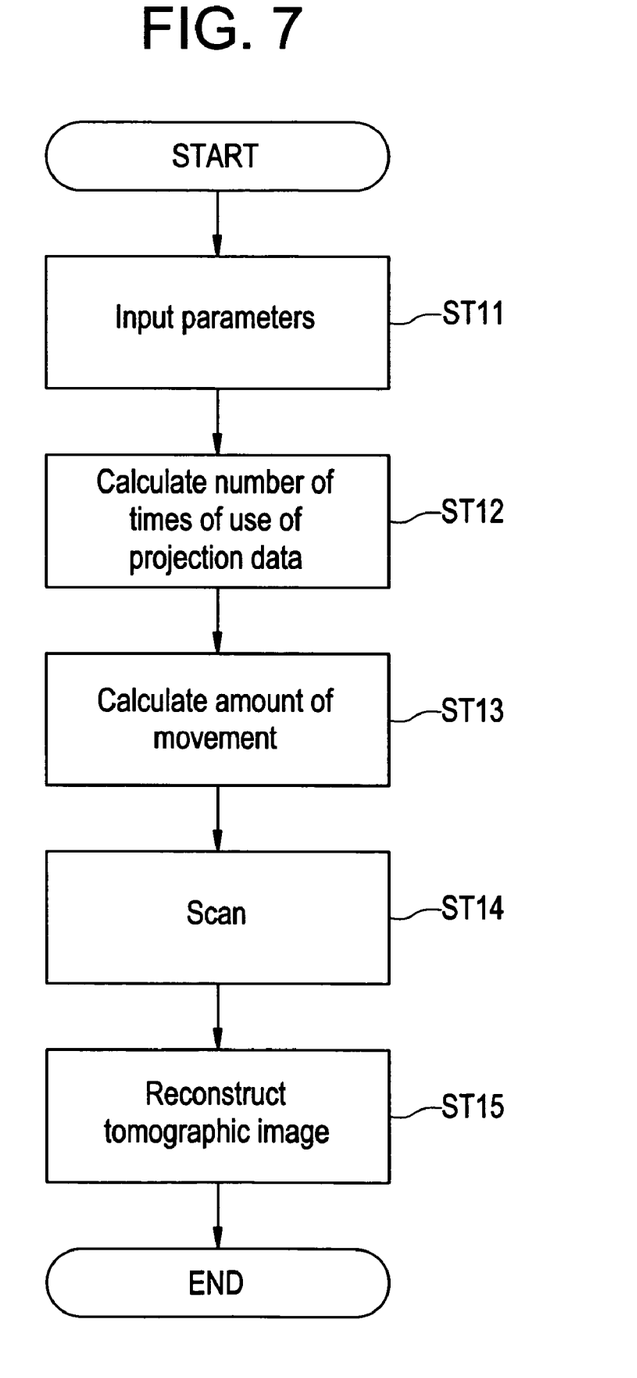
FIG. 7 is a flow chart showing an image reconstruction procedure in accordance with the third embodiment of the present invention.

Now an image reconstruction procedure in the third embodiment will be summarized with reference to a flow chart shown in FIG. 7.

Similarly to the aforementioned embodiments, parameters relating to imaging, such as the position and size of a tomographic image Im to be obtained and the helical pitch, are first input (Step ST11).

These parameters relating to imaging are stored together with parameters relating to the apparatus configuration in the storage device 33 as the parameters relating to reconstruction of tomographic image data.

The control section 34 arithmetically determines how many sets of projection data are to be used to reconstruct tomographic image data for a tomographic image Im at a certain position based on the parameters relating to reconstruction of tomographic image data (Step ST12).

From the standpoint of projection data, the number of times of use of the projection data in tomographic image data is determined.

The control section 34 determines the amount of movement of the rotating section 27 relative to the subject 6 so that the number of times of use of projection data reaches the number calculated at Step ST12 (Step ST13).

Since the helical pitch determines the movement speed of the imaging table 4 and the rotation speed of the rotating section 27, the amount of movement of the rotating section 27 is determined by the rotation angle of the rotating section 27 from the scan start position.

Then, a helical scan is conducted so that the rotating section 27 attains the amount of movement calculated at Step ST13. (Step ST14).

At that time, X-rays are set so that they impinge on all detector rows in the detector array 23.

The reconstructing section 36 reconstructs image data for the tomographic image Im based on detected data acquired in the helical scan at Step ST4 using the data the number of times of use calculated at Step ST12. (Step ST15).

The tomographic image data is reconstructed using the cone BP process known in the art, for example.

The tomographic image Im having image data reconstructed by the calculation by the reconstructing section 36 is displayed on the display device 32 as needed.

As described above, in the third embodiment, the number of times of use of projection data for reconstructing tomographic image data is determined based on parameters relating to reconstruction of the tomographic image data at a certain position. Moreover, the amount of movement of the rotating section 27 is determined so that projection data corresponding to the number of times of use in reconstruction are acquired.

Thus, the number of times of use of projection data acquired by detector rows near the ends in the z-direction is increased in reconstruction of image data for the tomographic image Im. Consequently, radiation emitted from the X-ray tube 20 is efficiently used.

Projection data acquired by detector rows near the ends are those acquired at a position away from the tomographic image Im in the z-direction. Therefore, if such projection data is used to reconstruct the tomographic image Im, the image quality of the tomographic image Im is not reduced but is not always improved. However, by using the projection data acquired by detector rows near the ends, information on the tomographic image Im is increased accordingly, and definite improvement of the S/N (signal-to-noise) ratio can be expected, resulting in improved reproducibility of the tomographic image Im.

Furthermore, in the third embodiment, the collimator does not need to be controlled in acquiring projection data. Thus, the configuration and control of the X-ray CT apparatus are simplified.

It should be noted that the present invention is not limited to the aforementioned embodiments, and may be appropriately modified within the scope of the appended claims. For example, radiation for use in scanning is not limited to X-rays but may be other radiation such as gamma rays. Moreover, tomographic image data may be reconstructed by some other image reconstruction technique than the cone BP process, provided only that projection data is acquired by a detector array having a plurality of detector rows in a direction along the axis of rotation AX.

Furthermore, the rotating section 27, instead of the imaging table 4, may be moved in the z-direction, provided only that the subject 6 and rotating section 27 are movable relative to each other in the direction of the axis of rotation AX.

Many widely different embodiments of the invention may be configured without departing from the spirit and the scope of the present invention. It should be understood that the present invention is not limited to the specific embodiments described in the specification, except as defined in the appended claims.

The invention claimed is:

1. A radiation computed tomography apparatus comprising:
   a radiation source for emitting radiation toward a subject;
   an adjusting device for adjusting an emission extent of the radiation from said radiation source in response to a control command;
   a detector array forming a two-dimensional radiation detection surface comprised of a plurality of radiation detectors, for detecting the radiation on said radiation detection surface;
   a reconstructing device for calculating and reconstructing tomographic image data for a tomographic image of said subject based on projection data of said subject by the radiation acquired by said detector array; and
   a control device for calculating an irradiated region in said radiation detection surface required for acquiring said projection data for use in reconstruction of a certain portion of said tomographic image data based on parameters relating to reconstruction of said tomographic image data by said reconstructing device, and outputting control command to said adjusting device for emitting the radiation to impinge upon said irradiated region, wherein said control device configured to calculate the irradiation region by selecting a subset from a set of rows of said radiation detectors, and said control device configured to select the subset based on the parameters including a helical pitch of a helical scan.

2. The radiation computed tomography apparatus of claim 1, wherein:
   said apparatus further comprises a moving device supporting said radiation source, adjusting device and detector array while maintaining their relative positional relationship; and
   said moving device rotates said radiation source, adjusting device and detector array around a predefined axis with respect to said subject while moving them relative to said subject in said axis direction.

3. The radiation computed tomography apparatus of claim 2, wherein:
   said control device outputs said control command to said adjusting device for emitting the radiation to constantly impinge upon said irradiated region during movement of said moving device.

4. The radiation computed tomography apparatus of claim 2, wherein:
   said control device causes the radiation to impinge upon a partial irradiated region within said irradiated region, and outputs a control command to said adjusting device for consecutively changing the position of said partial irradiated region as said moving device moves.

5. The radiation computed tomography apparatus of claim 4, wherein:
   said partial irradiated region is a region upon which the radiation impinges passing through said subject corresponding to a certain portion of said tomographic image during movement of said moving device.

6. The radiation computed tomography apparatus of claim 2 wherein:
   said moving device rotates said radiation source, adjusting device and detector array around a predefined axis with respect to said subject while moving them relative to said subject in said axis direction at the helical pitch that is one or less.

7. The radiation computed tomography apparatus of claim 6, wherein:
   said parameters include the size of said tomographic image, the position of said tomographic image with respect to said axis, the number of said radiation detectors in a direction along said axis, the positional relationship between said radiation source and said detector array, and said helical pitch.

8. The radiation computed tomography apparatus of claim 2, wherein:
   said tomographic image data is reconstructed at a midpoint of a distance of movement of said moving device relative to said subject during one rotation, based on said projection data for one rotation of said moving device around said axis.

9. A radiation computed tomography apparatus comprising:
   a radiation source for emitting radiation having a predefined width toward a subject;
   a detector array forming a two-dimensional radiation detection surface comprised of a plurality of radiation detectors, for detecting the radiation on said radiation detection surface, wherein said apparatus configured to calculate and reconstruct tomographic image data for a tomographic image of said subject based on projection data of said subject by the radiation from said radiation source acquired by said detector array; and
   a processing device for, in reconstruction of said tomographic image data, determining the number of times of use of said projection data from each of said plurality of radiation detectors based on parameters relating to reconstruction of said tomographic image data.

10. The radiation computed tomography apparatus of claim 9, wherein:
    said apparatus further comprises a moving device supporting said radiation source and detector array while maintaining their relative positional relationship; and
    said moving device rotates said radiation source and detector array around a predefined axis with respect to said subject while moving them relative to said subject in said axis direction.

11. The radiation computed tomography apparatus of claim 10, wherein:
    the radiation is emitted to constantly impinge upon whole of said radiation detection surface during movement of said moving device.

12. The radiation computed tomography apparatus of claim 10, further comprising:

a calculating device for determining the amount of movement of said moving device according to said number of times of use determined by said processing device.

13. The radiation computed tomography apparatus of claim 12, wherein:

said calculating device determines a rotation angle of said moving device so that said projection data for said number of times of use determined according to said parameters are acquired by each of said radiation detectors.

14. The radiation computed tomography apparatus of claim 13, wherein:

said tomographic image data is reconstructed at a midpoint of a distance of movement of said moving device relative to said subject during a rotation by said rotation angle determined by said calculating device.

15. The radiation computed tomography apparatus of claim 10, wherein:

said moving device rotates said radiation source, adjusting device and detector array around a predefined axis with respect to said subject while moving them relative to said subject in said axis direction at a helical pitch that is one or less.

16. The radiation computed tomography apparatus of claim 15, wherein:

said parameters include the size of said tomographic image, the position of said tomographic image with respect to said axis, the number of said radiation detectors in a direction along said axis, the positional relationship between said radiation source and said detector array, and said helical pitch.

* * * * *

UNITED STATES PATENT AND TRADEMARK OFFICE
CERTIFICATE OF CORRECTION

PATENT NO. : 7,076,019 B2  Page 1 of 1
APPLICATION NO. : 10/828456
DATED : July 11, 2006
INVENTOR(S) : Hagiwara et al.

It is certified that error appears in the above-identified patent and that said Letters Patent is hereby corrected as shown below:

In Claim 1, column 13, line 37, between "outputting" and "control", insert -- a --.

Signed and Sealed this

Seventeenth Day of June, 2008

JON W. DUDAS
*Director of the United States Patent and Trademark Office*